(12) United States Patent
Igarashi (10) Patent No.: US 11,786,905 B2
(45) Date of Patent: Oct. 17, 2023

(54) BLOOD COMPONENT SEPARATION APPARATUS WITH INTERNAL PRESSURE MONITOR

(71) Applicant: TERUMO KABUSHIKI KAISHA, Tokyo (JP)

(72) Inventor: Masatsugu Igarashi, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 68 days.

(21) Appl. No.: 17/426,868

(22) PCT Filed: Jan. 17, 2020

(86) PCT No.: PCT/JP2020/001490
§ 371 (c)(1),
(2) Date: Jul. 29, 2021

(87) PCT Pub. No.: WO2020/158454
PCT Pub. Date: Aug. 6, 2020

(65) Prior Publication Data
US 2022/0105517 A1    Apr. 7, 2022

(30) Foreign Application Priority Data

Feb. 1, 2019  (JP) ................................. 2019-016766

(51) Int. Cl.
*B01L 3/00* (2006.01)

(52) U.S. Cl.
CPC .......... *B01L 3/56* (2013.01); *B01L 2200/0689* (2013.01); *B01L 2200/146* (2013.01);
(Continued)

(58) Field of Classification Search
CPC ............ A61M 1/02; A61M 2205/3331; A61M 2205/3393; B01L 2200/0689;
(Continued)

(56) References Cited

U.S. PATENT DOCUMENTS

| 4,285,464 A | 8/1981 | Latham, Jr. |
| 4,464,172 A | 8/1984 | Lichtenstein |

(Continued)

FOREIGN PATENT DOCUMENTS

| JP | H08-506977 | 7/1996 |
| JP | 2002-513321 | 5/2002 |

(Continued)

OTHER PUBLICATIONS

International Searching Authority, International Search Report and Written Opinion, PCT/JP2020/0014909; dated Apr. 21, 2020, 10 pages.

(Continued)

*Primary Examiner* — Jennifer Wecker
*Assistant Examiner* — Jonathan Bortoli
(74) *Attorney, Agent, or Firm* — Sheridan Ross P.C.

(57) ABSTRACT

A blood component collection cassette of a blood component collection system, which is a biological component transfer system, includes a sheet-shaped cassette main body in which a blood line is formed. The blood line includes a second applied load measurement unit and line main body portions. A separation device includes a second load measurement unit that measures a load applied to a wall portion of the second applied load measurement unit in a cassette mounted state. The second applied load measurement unit is more easily deformed than the line main body portions, and is disposed at a location within the blood line on which only a positive pressure acts.

17 Claims, 10 Drawing Sheets

(52) U.S. Cl.
CPC ............... *B01L 2300/0663* (2013.01); *B01L 2300/0864* (2013.01); *B01L 2300/14* (2013.01); *B01L 2400/0478* (2013.01)

(58) Field of Classification Search
CPC ....... B01L 2200/146; B01L 2300/0663; B01L 2300/0864; B01L 2300/14; B01L 2400/0478; B01L 3/56
See application file for complete search history.

(56) References Cited

U.S. PATENT DOCUMENTS

| | | |
|---|---|---|
| 2006/0028909 A1 | 2/2006 | Behague |
| 2006/0155236 A1 | 7/2006 | Gara et al. |
| 2007/0004997 A1 | 1/2007 | Felt et al. |
| 2017/0319086 A1* | 11/2017 | Masuda ............. A61B 5/02241 |
| 2017/0340255 A1* | 11/2017 | Jung ................ A61B 5/150755 |
| 2019/0060547 A1* | 2/2019 | Kusters ............... A61M 1/3496 |
| 2019/0231949 A1* | 8/2019 | Igarashi .............. A61M 1/0245 |

FOREIGN PATENT DOCUMENTS

| | | |
|---|---|---|
| JP | 2002-527212 | 8/2002 |
| JP | 2006-175232 | 7/2006 |
| WO | WO 94/19031 | 9/1994 |
| WO | WO 00/23140 | 4/2000 |
| WO | WO 2016/068213 | 5/2016 |
| WO | WO 2018/230155 | 12/2018 |

OTHER PUBLICATIONS

Official Action with English Translation for Japan Patent Application No. 2021-51911, dated May 9, 2023, 10 pages.
Official Action with English Translation for Japan Patent Application No. 2021-519911, dated Aug. 8, 2023, 11 pages.

* cited by examiner

BLOOD COMPONENT SEPARATION APPARATUS WITH INTERNAL PRESSURE MONITOR

TECHNICAL FIELD

The present invention relates to a system used for separating and culturing a biological component, and more particularly to a biological component transfer system.

BACKGROUND ART

In blood donation in recent years, in addition to whole blood collection in which whole blood is collected from blood donors, component blood sampling (apheresis) has been performed in which the burden on the blood donor's body is made lighter. Component blood sampling is a blood collection method in which a blood component collection system (apheresis system) is used, whereby only specific blood components are collected from whole blood, and the remaining blood components are returned again into the donor's body.

Further, cell therapy, which is a treatment method for treating diseases using patients' own cells or cells from other people, has come to be performed as a new medical treatment. In cell therapy, the cells that are used for therapy are collected and cultured using a culture apparatus or the like.

In Japanese Laid-Open Patent Publication No. 2013-514863 (PCT), a blood component collection system is disclosed in which blood platelets are collected by centrifugally separating whole blood that is extracted from a blood donor. Such a blood component collection system includes a blood collection circuit set, which forms a circuit through which blood or blood components to be treated flow, and a centrifugal separation device (blood component separation device) on which the blood collection circuit set is mounted.

The blood collection circuit set is equipped with a blood collection line having a blood collection needle, a band-shaped channel (separator) into which whole blood is introduced, a plurality of bags for accommodating the blood components, etc., and a cassette connected through a plurality of tubes to the line, the channel, and the bags. A plurality of flow paths, including a line for introducing blood from a blood donor, a line for transferring the blood components into a bag, a blood returning line for returning uncollected blood components to the donor, etc., are formed in the cassette. When used, the cassette is mounted in a mounting unit disposed in the blood component separation device.

SUMMARY OF INVENTION

In such a blood component collection system, in order to ascertain whether or not the blood component separation device is operating properly, it is necessary to measure and monitor the pressure (circuit internal pressure) inside the blood collection circuit. The same problem exists in the biological component transfer system used for the separation and culture of biological components (for example, cells) other than in a blood component collection system.

The present invention has been devised taking into consideration the aforementioned problems, and has the object of providing a biological component transfer system which is capable of accurately measuring the circuit internal pressure.

One aspect of the present invention is characterized by a biological component transfer system including a biological component transfer device configured to be used for transferring a predetermined biological component within a biological fluid, and an apparatus to which the biological component transfer device is attached, wherein the biological component collection device includes a sheet-shaped device main body in which a biological fluid line is formed, the biological fluid line including an applied load measurement unit having a wall portion made of a soft material, and a line main body portion connected to the applied load measurement unit, wherein the apparatus includes a load measurement unit configured to measure a load applied to the wall portion of the applied load measurement unit in a device mounted state in which the biological component transfer device is attached to the apparatus, and the applied load measurement unit is more easily deformed than the line main body portion, and is disposed at a location within the biological fluid line on which only a positive pressure acts.

According to the present invention, since the applied load measurement unit is disposed at a location where only a positive pressure acts on the biological fluid line, the applied load measurement unit is not blocked or obstructed due to a negative pressure. Further, since the applied load measurement unit is more easily deformed than the line main body portion, creep deformation of the applied load measurement unit (a reduction in the reaction force of the applied load measurement unit over time) can be suppressed. Accordingly, the circuit internal pressure can be measured with high accuracy.

DESCRIPTION OF EMBODIMENTS

Hereinafter, a preferred embodiment of a biological component transfer system according to the present invention will be presented and described in detail below with reference to the accompanying drawings.

Figure 1:
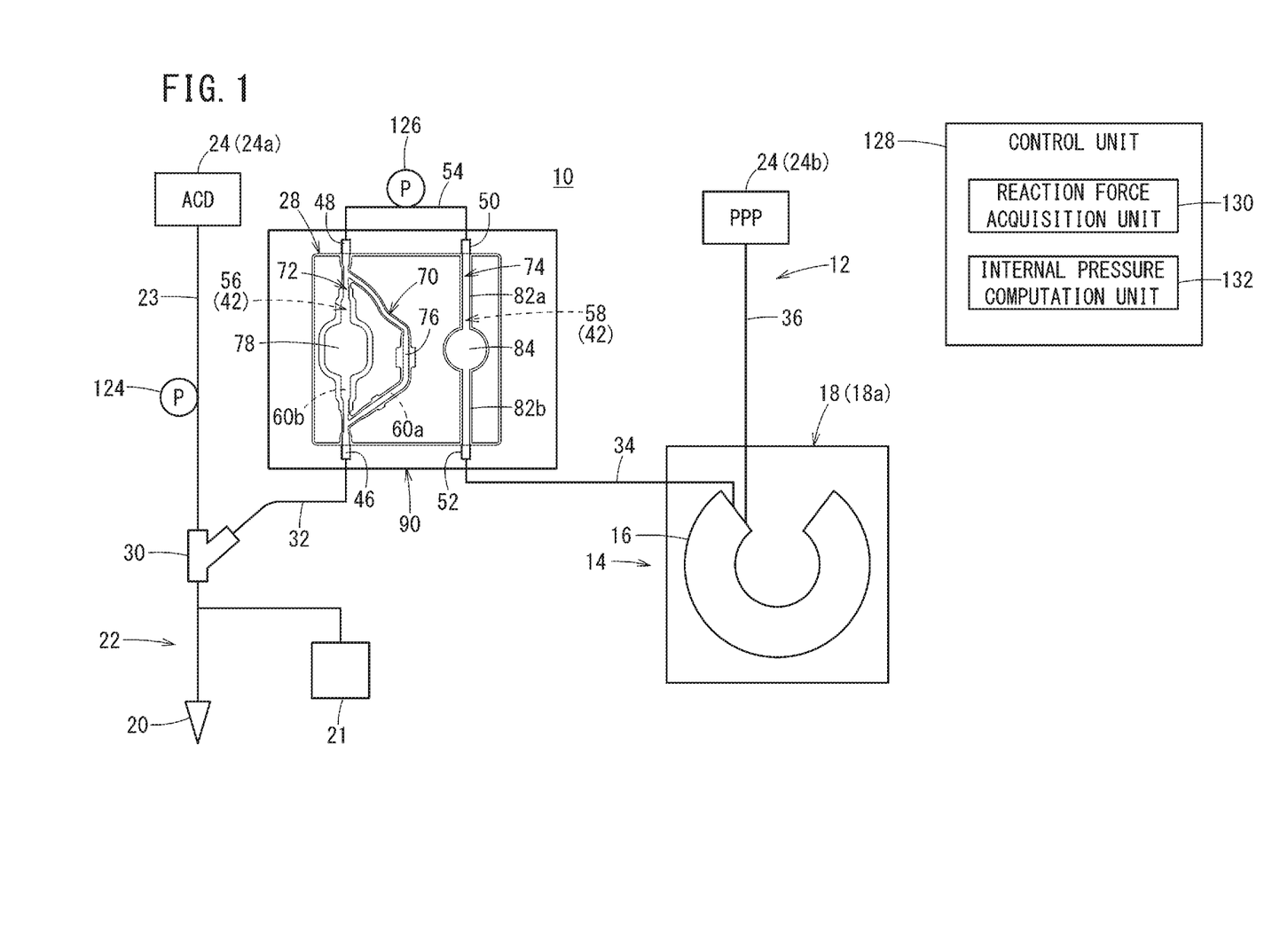
FIG. 1 is a schematic diagram of a blood component collection system according to an embodiment of the present invention.

In FIG. 1, a blood component collection system 10, which is a form of the biological component transfer system according to the present invention, is configured as a blood apheresis system. More specifically, in the blood component collection system 10, by continuously removing blood (whole blood) from a donor (blood donor) and centrifuging the blood outside of the body, a specific blood component (in the present embodiment, plasma [platelet poor plasma: PPP]) is collected, and the remaining blood components are returned to the donor.

First, an outline description will be given of the blood component collection system 10 shown in FIG. 1. The blood component collection system 10 is equipped with a blood collection circuit set 12 (collection circuit set) for enabling storage and flow of blood components therein, and a separation device 14 that separates the blood components from the blood. The blood collection circuit set 12 includes a blood treatment unit 16 (biological fluid treatment unit) in which whole blood that is removed from the donor is centrifugally separated into a plurality of blood components. The separation device 14 is a centrifugal separation device that applies centrifugal force to the blood collection circuit set 12. The separation device 14 is equipped with a separation processing unit 18 (centrifuge unit) having a rotor 18a for applying a centrifugal force to the blood treatment unit 16.

The blood collection circuit set 12 is discarded every time that it is used in order to prevent contamination and ensure sanitation. The blood collection circuit set 12 includes a collection and returning unit 22 having a blood collection needle 20 and an initial flow blood collection bag 21, the blood treatment unit 16, a plurality of bags 24, and a blood component collection cassette 28 (hereinafter referred to as a "cassette 28"). The plurality of bags 24 include an ACD solution bag 24a containing an ACD solution which is an anticoagulant, and a PPP bag 24b for storing the plasma (platelet poor plasma).

The collection and returning unit 22 is connected to the ACD solution bag 24a and the cassette 28 via a tube connector 30. The ACD solution bag 24a is connected to the tube connector 30 via an ACD solution transfer tube 23.

The cassette 28 which is the biological component transfer device is configured to be attachable to the separation device 14. Stated otherwise, the separation device 14 is a device in which the cassette 28 is mounted. The cassette 28 is connected to the collection and returning unit 22 via a donor side tube 32, and is also connected to the blood treatment unit 16 via a treatment unit side tube 34. The blood treatment unit 16 is attached to the separation processing unit 18 (rotor 18a) of the separation device 14, and is configured in the form of a container in which blood can be introduced therein, flow therethrough, and flow out therefrom. The PPP bag 24b is connected to the blood treatment unit 16 via a PPP transfer tube 36.

Figure 2:
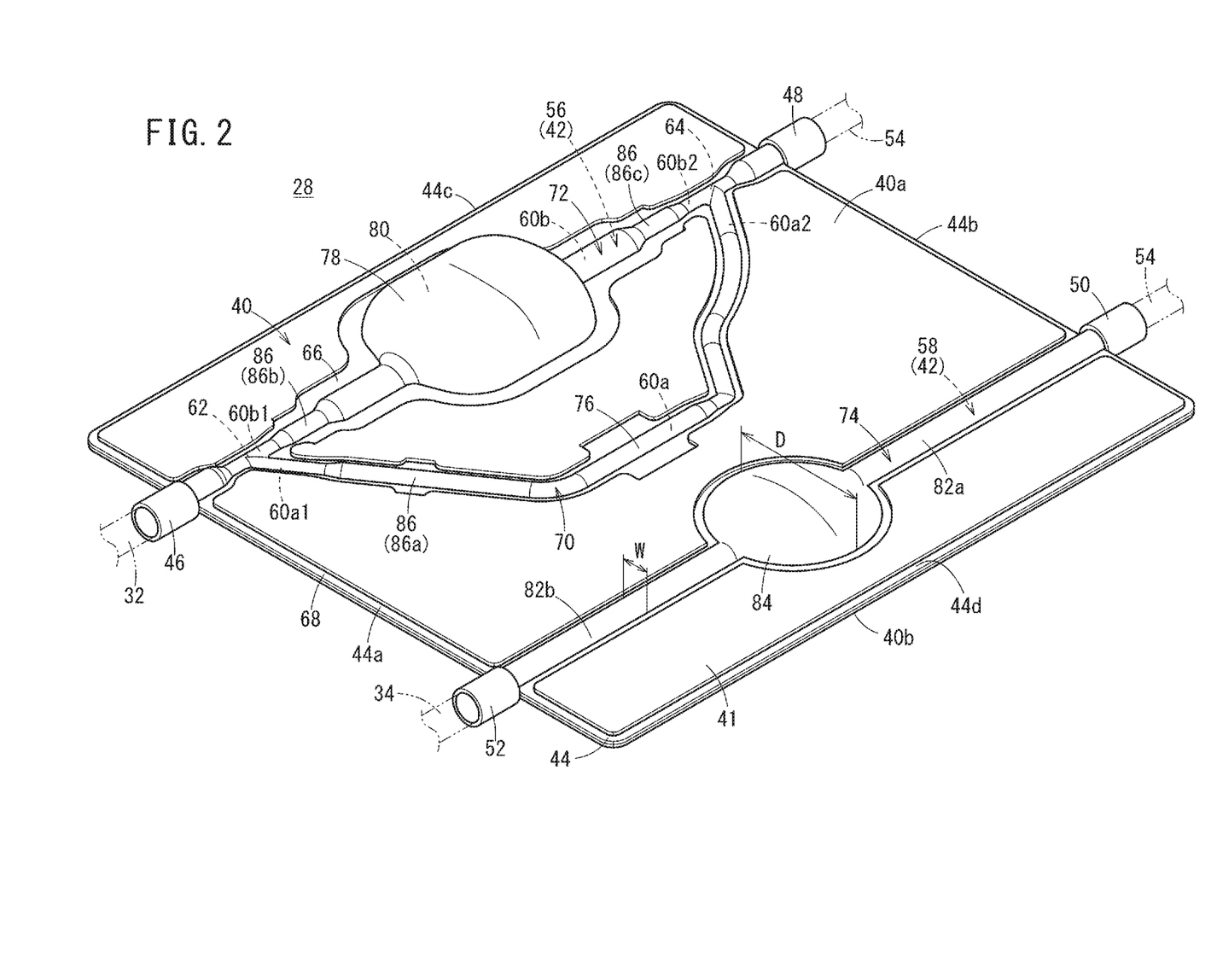
FIG. 2 is a perspective view of a blood component collection cassette.

As shown in FIG. 2, the cassette 28 is provided with a cassette main body 40 (device main body) in which a blood line 42 (biological fluid line) is formed through which blood or blood components flow.

The cassette main body 40 is formed of a soft material in a sheet-like shape, and is configured in a quadrangular shape when viewed in plan. For the soft material that constitutes the cassette main body 40, the same material is used over the entirety of the cassette main body 40. Moreover, the cassette main body 40 may be constituted from a plurality of different materials. More specifically, the cassette main body 40 includes a first sheet 40a and a second sheet 40b formed of a soft material. The first sheet 40a and the second sheet 40b are stacked in a thickness direction and are joined to each other.

As examples of the soft material that constitutes the first sheet 40a and the second sheet 40b, there may be cited vinyl chloride, polyolefin, polyurethane, and the like. As examples of a vinyl chloride plasticizer, there may be cited diisononylcyclohexane-1,2-dicarboxylate, bis-2-ethylhexyl phthalate, and the like.

The blood line 42 is formed between the first sheet 40a and the second sheet 40b. Fusion bonding (high frequency fusion bonding, thermal fusion bonding, etc.) is used as the means for joining the first sheet 40a and the second sheet 40b. The first sheet 40a and the second sheet 40b may also be joined together by another joining means (adhesion or the like).

The outer peripheral edge portion 44 of the cassette main body 40 includes a first edge portion 44a and a second edge portion 44b that extend in parallel with each other, and a third edge portion 44c and a fourth edge portion 44d that extend in parallel with each other. The directions in which the first edge portion 44a and the second edge portion 44b extend are orthogonal to the directions in which the third edge portion 44c and the fourth edge portion 44d extend.

A first port member 46, a second port member 48, a third port member 50, and a fourth port member 52, which are made of a hard material (for example, vinyl chloride, polypropylene, polycarbonate, or the like), are provided on the outer peripheral edge portion 44 of the cassette main body 40. The first port member 46 and the fourth port member 52 are disposed on the first edge portion 44a, and the second port member 48 and the third port member 50 are disposed on the second edge portion 44b.

The donor side tube 32 is connected to the first port member 46. One end of a connection tube 54 is connected to the second port member 48. The other end of the connection tube 54 is connected to the third port member 50. The connection tube 54 is made of a soft material. A pump 126, to be described later, is provided in the connection tube 54 (see FIG. 1). A treatment unit side tube 34 is connected to the fourth port member 52.

According to the present embodiment, the first port member 46 and the second port member 48 are disposed on the same straight line along the direction in which the third edge portion 44c and the fourth edge portion 44d extend. It should be noted that the first port member 46 and the second port member 48 need not necessarily be arranged on the same straight line. The third port member 50 and the fourth port member 52 are disposed on the same straight line along the direction in which the third edge portion 44c and the fourth edge portion 44d extend. It should be noted that the third port member 50 and the fourth port member 52 need not necessarily be arranged on the same straight line.

The blood line 42 includes a donor side line 56 located on the side of the third edge portion 44c of the cassette main body 40, and a separation side line 58 located on the side of the fourth edge portion 44d of the cassette main body 40. The donor side line 56 and the separation side line 58 are in communication with each other via the connection tube 54. The donor side line 56 forms a portion of the flow path between the pump 126 and the donor (see FIG. 1). The first port member 46 is connected to one end of the donor side line 56, and the second port member 48 is connected to the other end of the donor side line 56.

The donor side line 56 includes a blood collection line 60a (first line) through which the blood is made to flow at a time of blood collection, and a blood returning line 60b (second line) through which the blood components are made to flow at a time that the blood is returned. One end portion 60a1 of the blood collection line 60a and one end portion 60b1 of the blood returning line 60b are connected mutually via a first coupling member 62. Another end portion 60a2 of the blood collection line 60*a* and another end portion 60*b*2 of the blood returning line 60*b* are connected mutually via a second coupling member 64.

The blood collection line 60*a* and the blood returning line 60*b* extend at least partially in parallel with each other. The first coupling member 62 and the second coupling member 64 each constitute parts of the donor side line 56.

The fourth port member 52 is connected to one end of the separation side line 58, and the third port member 50 is connected to the other end of the separation side line 58. The separation side line 58 is a flow path through which the blood and the blood components are made to flow, and forms a portion of the flow path between the pump 126 and the separation processing unit 18 (see FIG. 1). The separation side line 58 extends in a straight line along the direction in which the third edge portion 44*c* and the fourth edge portion 44*d* of the cassette main body 40 extend.

In the cassette main body 40, sealed portions 66 in the form of fusion-bonded locations are formed along the blood line 42 on both sides of the blood line 42. Further, a sealed portion 68 is formed along the outer peripheral edge portion 44, on the outer peripheral edge portion 44 of the cassette main body 40. In the cassette main body 40 (excluding the convex portion that forms the blood line 42), locations other than the sealed portions 66 and 68 are non-sealed portions where the first sheet 40*a* and the second sheet 40*b* are not fusion bonded to each other. Since the sealed portions 66 and 68 are subjected to pressure during formation thereof, the sealed portions 66 and 68 are smaller in thickness than the non-sealed portions, and are recessed with respect to the non-sealed portions. Stated otherwise, the non-sealed portions protrude in the thickness direction with respect to the sealed portions 66 and 68.

Within the cassette main body 40, even when there is no positive pressure acting within the blood line 42, the wall portions that form the blood line 42 bulge in convex shapes in the thickness direction of the cassette 28 on both side surfaces of the cassette main body 40. Accordingly, the blood line 42 is a flow path which is opened in its natural state. When pressed by an external force, the wall portions can be elastically deformed in directions to close the blood line 42 at the pressed locations thereof.

The cassette main body 40 includes a blood collection line forming member 70 (first line forming member) that forms the blood collection line 60*a*, a blood returning line forming member 72 (second line forming member) that forms the blood returning line 60*b*, and a separation side line forming member 74 that forms the separation side line 58.

The blood collection line forming member 70 includes a first applied load measurement unit 76 (donor side load measurement unit) having a wall portion made of a soft material. The first applied load measurement unit 76 is a pressed part that is pressed by a later-described first load measurement unit 98 (see FIG. 3) which is installed in the separation device 14 in a cassette mounted state (device mounted state) in which the cassette 28 is mounted in the separation device 14. The first applied load measurement unit 76 constitutes a part of the wall portions of the blood collection line 60*a*. Accordingly, the first applied load measurement unit 76 bulges outwardly in the thickness direction of the cassette main body 40 from a sheet surface 41 (base surface) of the cassette main body 40.

The blood returning line forming member 72 includes a filter accommodating unit 78 which is made of a soft material. A filter member 80 for separating (removing) predetermined components (clotted blood or blood clumps) contained within the blood components is disposed inside the filter accommodating unit 78.

The separation side line forming member 74 has two individual line main body portions 82*a* and 82*b*, and a second applied load measurement unit 84 which is formed to be wider than the line main body portions 82*a* and 82*b*. The line main body portion 82*a* connects the third port member 50 and the second applied load measurement unit 84 to each other. The line main body portion 82*b* connects the second applied load measurement unit 84 and the fourth port member 52 to each other.

The second applied load measurement unit 84 includes a wall portion made of a soft material. The second applied load measurement unit 84 constitutes a part of the wall portions of the separation side line 58. Accordingly, the second applied load measurement unit 84 bulges outwardly in the thickness direction of the cassette main body 40 from a sheet surface 41 of the cassette main body 40.

The second applied load measurement unit 84 is disposed at a location within the blood line 42 where only a positive pressure acts. More specifically, since the separation side line 58 provided in the second applied load measurement unit 84 constitutes a portion of the flow path between the pump 126 and the separation processing unit 18, only a positive pressure acts thereon, and a negative pressure does not act thereon. The second applied load measurement unit 84 is formed in a circular shape as viewed in plan.

The second applied load measurement unit 84 is more easily deformed than the line main body portions 82*a* and 82*b*. According to the present embodiment, the second applied load measurement unit 84 is more easily deformed than the line main body portions 82*a* and 82*b*, due to being formed wider than the line main body portions 82*a* and 82*b*. The diameter D of the second applied load measurement unit 84 is preferably set to be greater than or equal to 150% of the width W of the line main body portions 82*a* and 82*b*. In this case, due to being increased in pressure, the second applied load measurement unit 84 can be made to bulge uniformly into a circular shape as viewed in plan.

Moreover, by setting the thickness of the wall portion constituting the second applied load measurement unit 84 to be thinner than the thickness of the wall portions constituting the line main body portions 82*a* and 82*b*, the second applied load measurement unit 84 may be more easily deformed than the line main body portions 82*a* and 82*b*. Alternatively, by constituting the second applied load measurement unit 84 with a material that is more flexible than the line main body portions 82*a* and 82*b*, the second applied load measurement unit 84 may be more easily deformed than the line main body portions 82*a* and 82*b*.

As the diameter D of the second applied load measurement unit 84 becomes larger, the measurement accuracy of the circuit internal pressure is improved. In the case that the wall portion of the second applied load measurement unit 84 is made of vinyl chloride together with the thickness of the wall portion of the second applied load measurement unit 84 being set to 0.6 mm, the diameter D of the second applied load measurement unit 84 is preferably set to be greater than or equal to 12 mm. However, the diameter D of the second applied load measurement unit 84 can be arbitrarily set. The optimum diameter D of the second applied load measurement unit 84 varies depending on the material and the thickness of the wall portion of the second applied load measurement unit 84. It is necessary for the diameter to be made smaller as the wall portion of the second applied load measurement unit 84 is softer, and for the diameter to be made larger as the wall portion is harder.

On the cassette 28, there are provided a plurality of clamp action members 86 (86a to 86c) on which a plurality of clamps 102 (102a to 102c) (see FIG. 3) which act as flow path opening/closing mechanisms are provided in the separation device 14. When the cassette 28 is installed in the separation device 14, the clamp action members 86 abut against or are placed in facing relation to their corresponding clamps 102. More specifically, the clamp action member 86a is disposed at a location forming a side of the first port member 46 of the blood collection line 60a in the cassette 28. The clamp action members 86b and 86c are disposed respectively at locations forming both sides of the filter accommodating unit 78 within the blood returning line 60b.

Moreover, the flow path structure formed in the cassette 28, and the number and arrangement of the provided bags 24 are not limited to the configurations shown and described above, but may be modified in accordance with the type of blood components to be collected, the method of use, and the like.

In FIG. 1, the separation device 14 is a device that is used repeatedly during blood component collection, and is provided, for example, in a medical facility, a blood collection vehicle, or the like. The separation device 14 is equipped with the separation processing unit 18 having the rotor 18a, and a cassette mounting unit 90 to which the cassette 28 of the blood collection circuit set 12 is capable of being attached.

Figure 3:
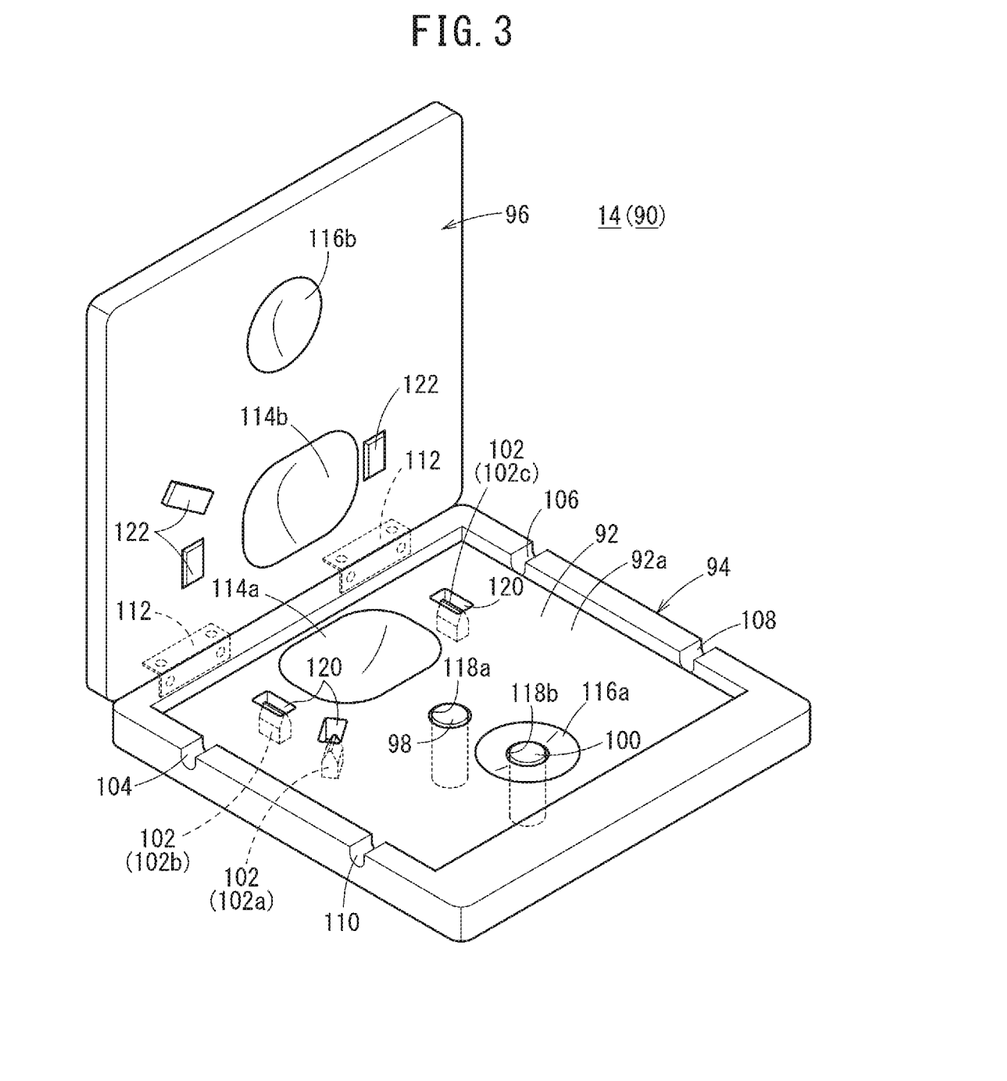
FIG. 3 is a perspective view of a cassette mounting unit.

As shown in FIG. 3, the cassette mounting unit 90 comprises an attachment base 94 in which a cassette mounting groove 92 is formed, a lid 96 that is capable of being opened and closed, a first load measurement unit 98 (donor side load measurement unit), a second load measurement unit 100 (separation side load measurement unit), and a plurality of clamps 102 (102a to 102c).

A first port arrangement groove 104 into which the first port member 46 of the cassette 28 can be arranged, a second port arrangement groove 106 into which the second port member 48 of the cassette 28 can be arranged, a third port arrangement groove 108 into which the third port member 50 of the cassette 28 can be arranged, and a fourth port arrangement groove 110 into which the fourth port member 52 of the cassette 28 can be arranged are provided on the outer peripheral portion of the attachment base 94. The first port arrangement groove 104, the second port arrangement groove 106, the third port arrangement groove 108, and the fourth port arrangement groove 110 communicate with the cassette mounting groove 92.

The lid 96 is configured so as to cover the attachment base 94 when closed, and is connected in a rotatable manner to the attachment base 94 via a hinge 112. When the lid 96 is closed with the cassette 28 being held in the cassette mounting groove 92 of the attachment base 94, the cassette 28 is sandwiched between the attachment base 94 and the lid 96. On the attachment base 94 and the lid 96, there are respectively provided concave portions 114a and 114b in which the filter accommodating unit 78 of the cassette 28 can be received.

Further, on the attachment base 94 and the lid 96, there are respectively provided concave portions 116a and 116b in which the second applied load measurement unit 84 of the cassette 28 can be received. Consequently, the cassette 28 is appropriately retained between the attachment base 94 and the lid 96, while also preventing the filter accommodating unit 78 and the second applied load measurement unit 84 from being crushed. Further, the concave portions 114a, 114b, 116a, and 116b prevent the filter accommodating unit 78 and the second applied load measurement unit 84 from bulging excessively.

The first load measurement unit 98 measures the load applied to a wall portion of the first applied load measurement unit 76 (see FIG. 2) in the cassette mounted state. The first load measurement unit 98 is configured to be capable of pressing the wall portion of the first applied load measurement unit 76 of the cassette 28. The first load measurement unit 98 is inserted into a first through hole 118a provided in the attachment base 94, together with being exposed in the cassette mounting groove 92. An upper surface of the first load measurement unit 98 protrudes from a bottom surface 92a of the cassette mounting groove 92.

The second load measurement unit 100 measures the load applied to a wall portion of the second applied load measurement unit 84 (see FIG. 2) in the cassette mounted state. The second load measurement unit 100 is configured to be capable of pressing the wall portion of the second applied load measurement unit 84 of the cassette 28. The second load measurement unit 100 is inserted into a second through hole 118b provided in the attachment base 94, together with being exposed in the cassette mounting groove 92. An upper surface of the second load measurement unit 100 protrudes from the bottom surface 92a of the cassette mounting groove 92. The first load measurement unit 98 and the second load measurement unit 100 are constituted from load cells, for example.

The plurality of clamps 102 are configured to be capable of pressing the clamp action members 86 (see FIG. 2) of the cassette 28. The plurality of clamps 102 (102a to 102c) are capable of being advanced and retracted in the thickness direction of the cassette 28 in a state in which the cassette 28 is retained in the cassette mounting groove 92, and are disposed corresponding to the arrangement of the plurality of clamp action members 86 (86a to 86c) provided on the cassette 28. The plurality of clamps 102 are capable of pressing the plurality of clamp action members 86, respectively, via a plurality of holes 120 that open on the bottom surface 92a of the cassette mounting groove 92. When closed, a plurality of projections 122 are provided on the lid 96 at positions corresponding to the plurality of holes 120 (clamps 102).

At a time that the clamp action members 86 are not being pressed by the clamps 102 in a state in which the cassette 28 is mounted in the cassette mounting unit 90, the flow paths inside the clamp action members 86 are opened. When the clamps 102 protrude from the holes 120 and press the clamp action members 86, the flow paths inside the clamp action members 86 are closed. In addition, when the clamps 102 are retracted, due to the elastic restorative force of (the clamp action members 86 of) the cassette main body 40, the clamp action members 86 are restored to their original shape, and the flow paths inside the clamp action members 86 are opened.

As shown in FIG. 1, the separation device 14 includes an ACD solution transfer pump 124 that operates on the ACD solution transfer tube 23, and a sampling or returning pump 126 that is connected to the cassette 28 and operates on the connection tube 54. The ACD solution transfer pump 124 is a pump that transfers the ACD solution from the ACD solution bag 24a to the cassette 28 and the blood treatment unit 16 via the ACD solution transfer tube 23. The pump 126 transfers the blood or the blood components. Stated otherwise, the pump 126 transfers the blood from the side of the donor to the blood treatment unit 16, together with transferring the blood components from the blood treatment unit 16 to the side of the donor. The ACD solution transfer pump 124 and the pump 126 are constituted, for example, by roller pumps or finger pumps.

The separation device 14 further includes a control unit 128. The control unit 128 is a computation device including a microcomputer, and has a CPU (central processing unit), and a ROM, a RAM, etc., serving as memories, wherein by reading out and executing programs stored in the ROM, the CPU functions as various function realizing units (function realizing means). Moreover, the various function realizing units may be constituted by function realizing devices in the form of hardware.

The control unit 128 controls operations of the above-described plurality of clamps 102. The control unit 128 includes a reaction force acquisition unit 130 and an internal pressure computation unit 132.

The reaction force acquisition unit 130 acquires the reaction forces of the first applied load measurement unit 76 and the second applied load measurement unit 84, before collection of the blood components is performed in which the blood or the blood components are made to flow through the blood line 42 in the cassette mounted state.

During collection of the blood components, the internal pressure computation unit 132 calculates the internal pressure (circuit internal pressure) of the first applied load measurement unit 76, on the basis of the reaction force of the first applied load measurement unit 76 as calculated by the reaction force acquisition unit 130, and the load detected by the first load measurement unit 98. During collection of the blood components, the internal pressure computation unit 132 calculates the internal pressure (circuit internal pressure) of the second applied load measurement unit 84, on the basis of the reaction force of the second applied load measurement unit 84 as calculated by the reaction force acquisition unit 130, and the load detected by the second load measurement unit 100.

Next, operations of the blood component collection system 10 according to the present embodiment, which is configured in the foregoing manner, will be described.

As a preparation (set-up) for collecting blood components from the donor using the blood component collection system 10 shown in FIG. 1, the blood collection circuit set 12 is attached to the separation device 14. More specifically, the cassette 28 is mounted in the cassette mounting unit 90, and the blood treatment unit 16 is attached to the rotor 18a. On the other hand, the blood collection needle 20 pierces (punctures) and is inserted into the donor.

Figure 4:
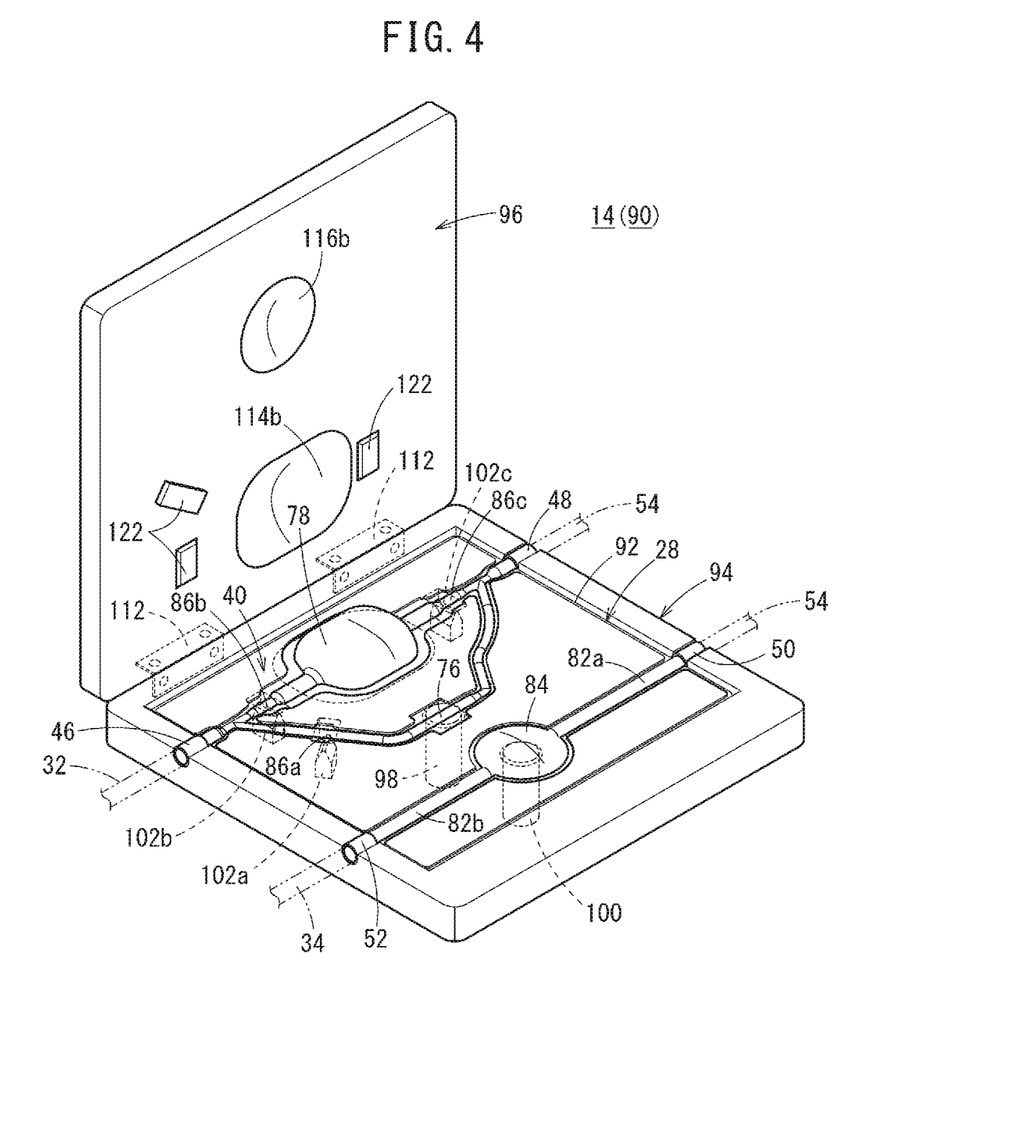
FIG. 4 is a perspective view of a cassette mounting unit in a state with the blood component collection cassette placed therein.

When the cassette 28 is mounted in the cassette mounting unit 90, as shown in FIG. 4, at first, the cassette 28 is mounted in the cassette mounting groove 92. In addition, by closing the lid 96, the cassette 28 is placed in a state of being held between the lid 96 and the attachment base 94. As a result, the first applied load measurement unit 76 and the second applied load measurement unit 84 of the cassette 28 are pressed respectively by the first load measurement unit 98 and the second load measurement unit 100, and are placed in a state of being slightly elastically deformed. Further, the plurality of clamp action members 86 of the cassette 28 are placed in facing relation with respect to the plurality of clamps 102.

When initiation of operations is instructed by an operation made by the user with respect to the separation device 14 shown in FIG. 1, in the separation device 14, under the action of the ACD solution transfer pump 124, priming with the ACD solution is carried out. More specifically, at a stage at which it is detected by a non-illustrated line sensor disposed outside of the cassette 28 that the ACD solution has arrived in the immediate vicinity of the first port member 46, priming by the ACD solution is terminated.

Next, by causing the rotor 18a to rotate, the separation device 14 applies a centrifugal force to the blood treatment unit 16 that is attached to the rotor 18a, and together therewith, by operation of the pump 126, blood (whole blood) from the donor is extracted and introduced into the blood treatment unit 16 (blood collection operation). By the centrifugal force that accompanies rotation of the rotor 18a, the blood introduced into the blood treatment unit 16 is separated into red blood cells (concentrated red blood cells), a buffy coat, and plasma (platelet poor plasma).

The plasma that is separated in the blood treatment unit 16 is introduced into the PPP bag 24b via the PPP transfer tube 36. After completion of the centrifugal separation process, the remaining blood components (the red blood cells and the buffy coat) are returned to the donor (returning operation). At this time, since foreign substances such as blood clumps and the like contained within the remaining blood components are trapped by the filter member 80 provided in the blood returning line 60b of the cassette 28, any risk caused by such foreign matter being returned to the donor can be reduced. The collection operation and the returning operation described above are performed a plurality of times.

During operation of the blood component collection system 10, the clamps 102 (see FIG. 3) of the separation device 14 are operated in the following manner.

Figure 5:
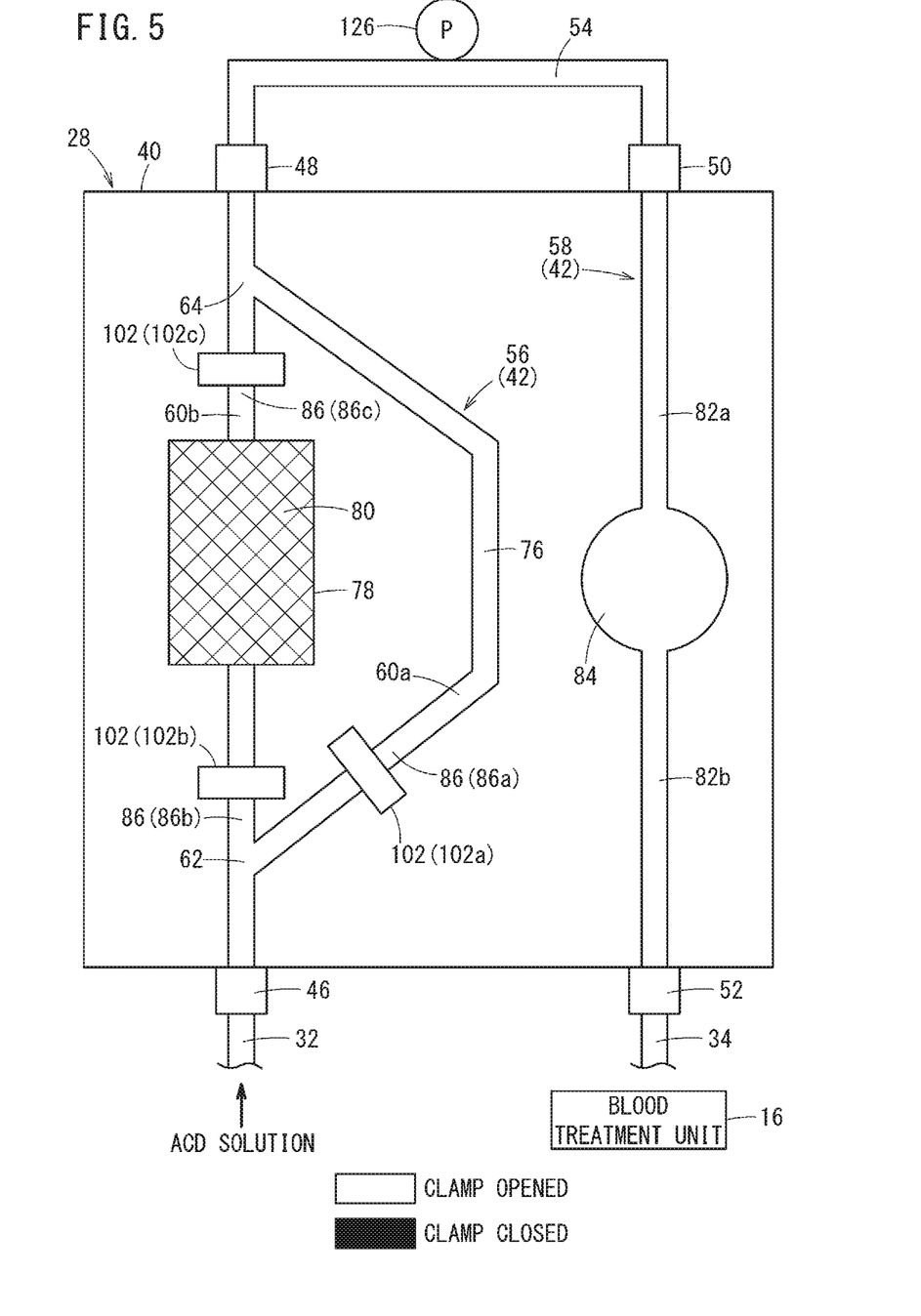
FIG. 5 is a first explanatory diagram illustrating the operation of clamps.

As shown in FIG. 5, when priming by the ACD solution is carried out, the clamps 102a, 102b, and 102c are opened. In addition, in this state, at a stage at which it is detected by the non-illustrated line sensor disposed outside of the cassette 28 in the immediate vicinity of the donor side line 56 that the ACD liquid has arrived in the vicinity of one end of the donor side line 56, priming with the ACD solution is terminated.

Figure 6:
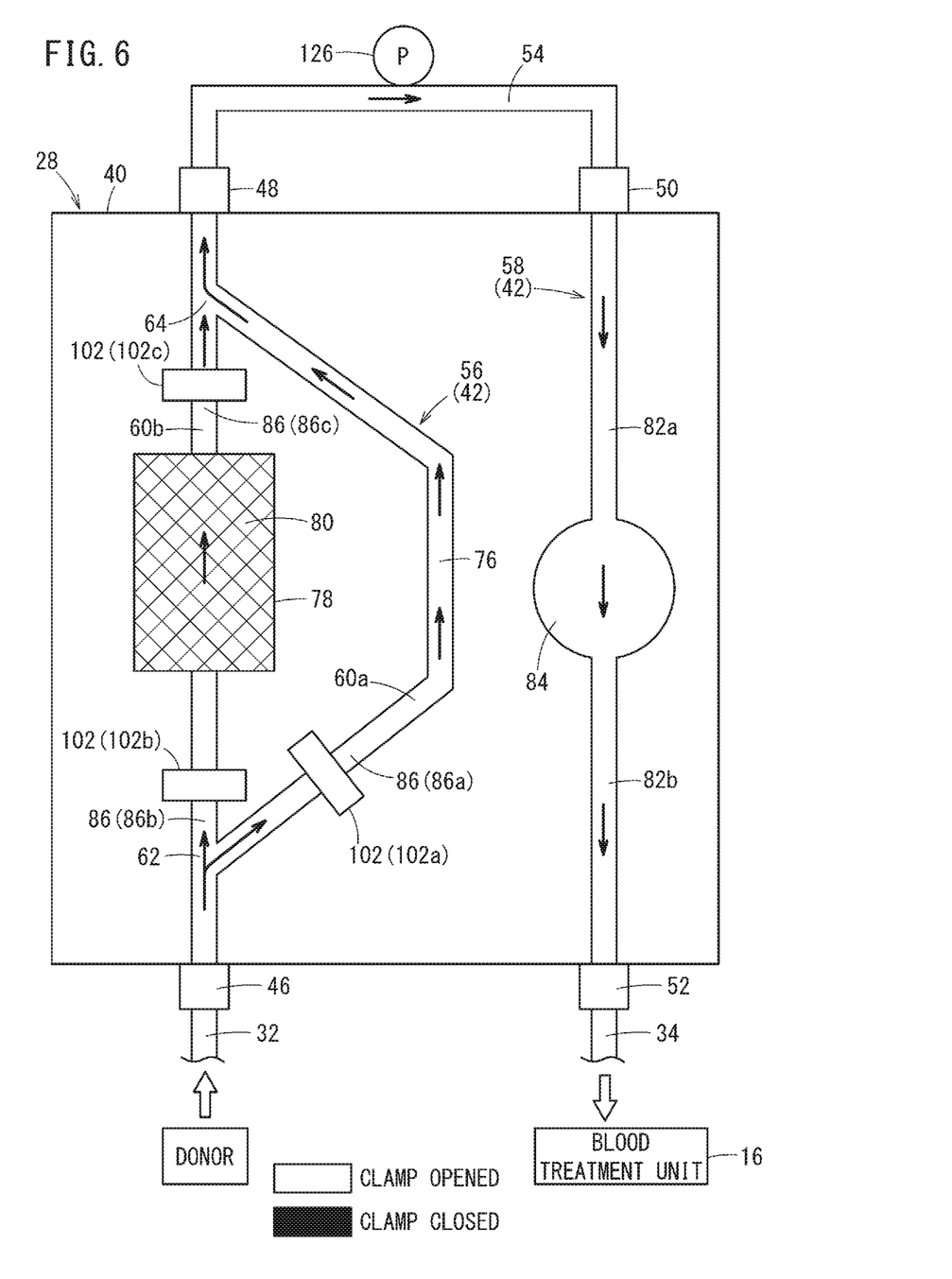
FIG. 6 is a second explanatory diagram illustrating the operation of clamps.

Next, when blood collection is performed for the first time, as shown in FIG. 6, the state in which the clamps 102a, 102b, and 102c are opened is maintained. In addition, in this state, blood from the donor is introduced into the blood line 42 of the cassette 28, and all of the air inside the circuit of the cassette 28 is pushed out by the blood into the blood treatment unit 16.

Figure 7:
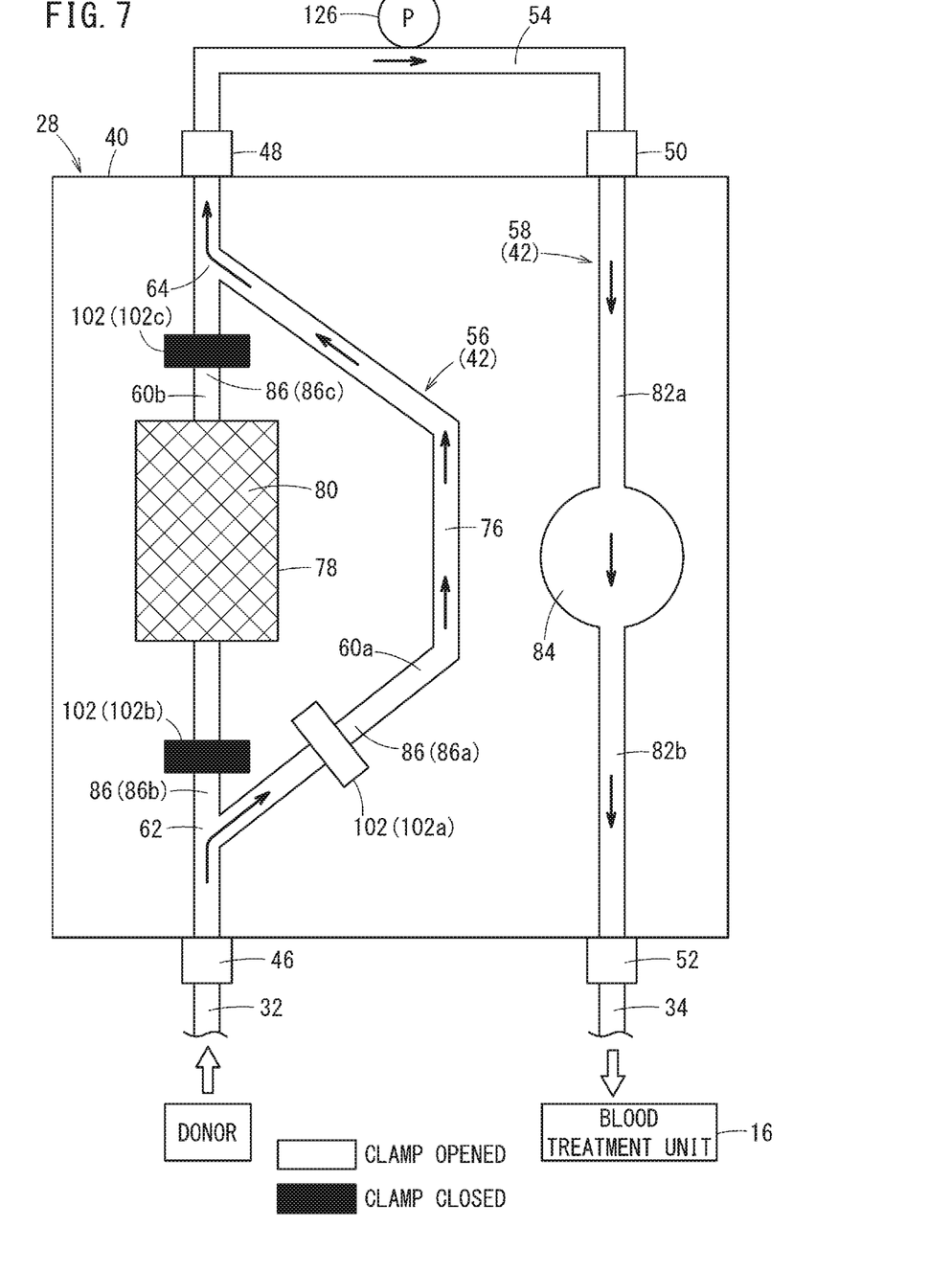
FIG. 7 is a third explanatory diagram illustrating the operation of clamps.

During the course of initial blood collection, as shown in FIG. 7, by closing the clamps 102b and 102c, the blood returning line 60b is closed. Consequently, a negative pressure is prevented from acting on the filter accommodating unit 78 and blocking the filter accommodating unit 78.

Figure 8:
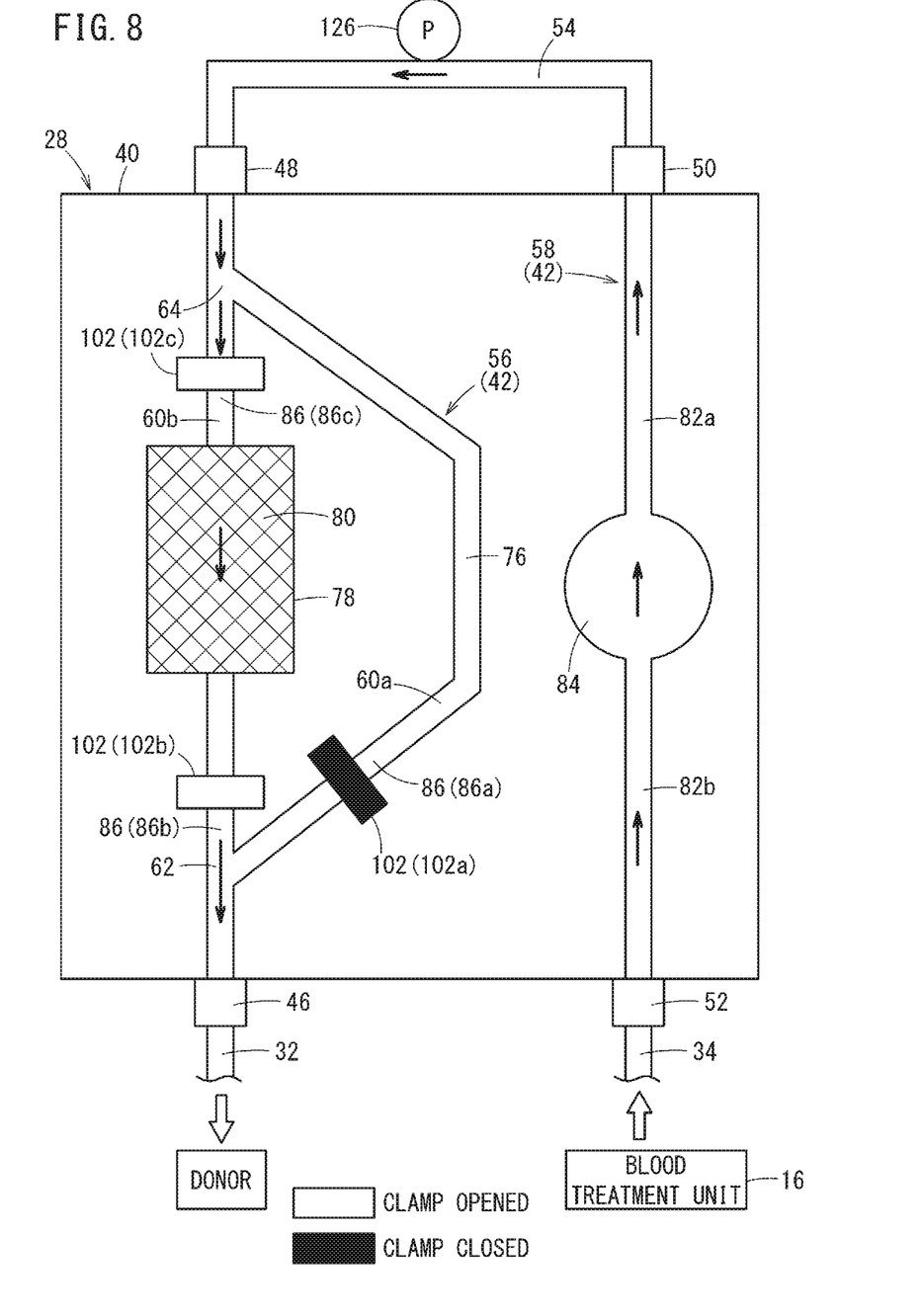
FIG. 8 is a fourth explanatory diagram illustrating the operation of clamps.

Next, when return of the blood components to the donor is carried out, as shown in FIG. 8, the clamp 102a is closed, and the clamps 102b and 102c are opened. Thus, the blood collection line 60a is closed, whereas the blood returning line 60b is opened. Accordingly, when the blood components pass through the filter member 80, clotted blood contained within the blood components is trapped in the filter member 80. Since the blood collection line 60a is closed, foreign matter cannot be returned to the donor via the blood collection line 60a.

Figure 9:
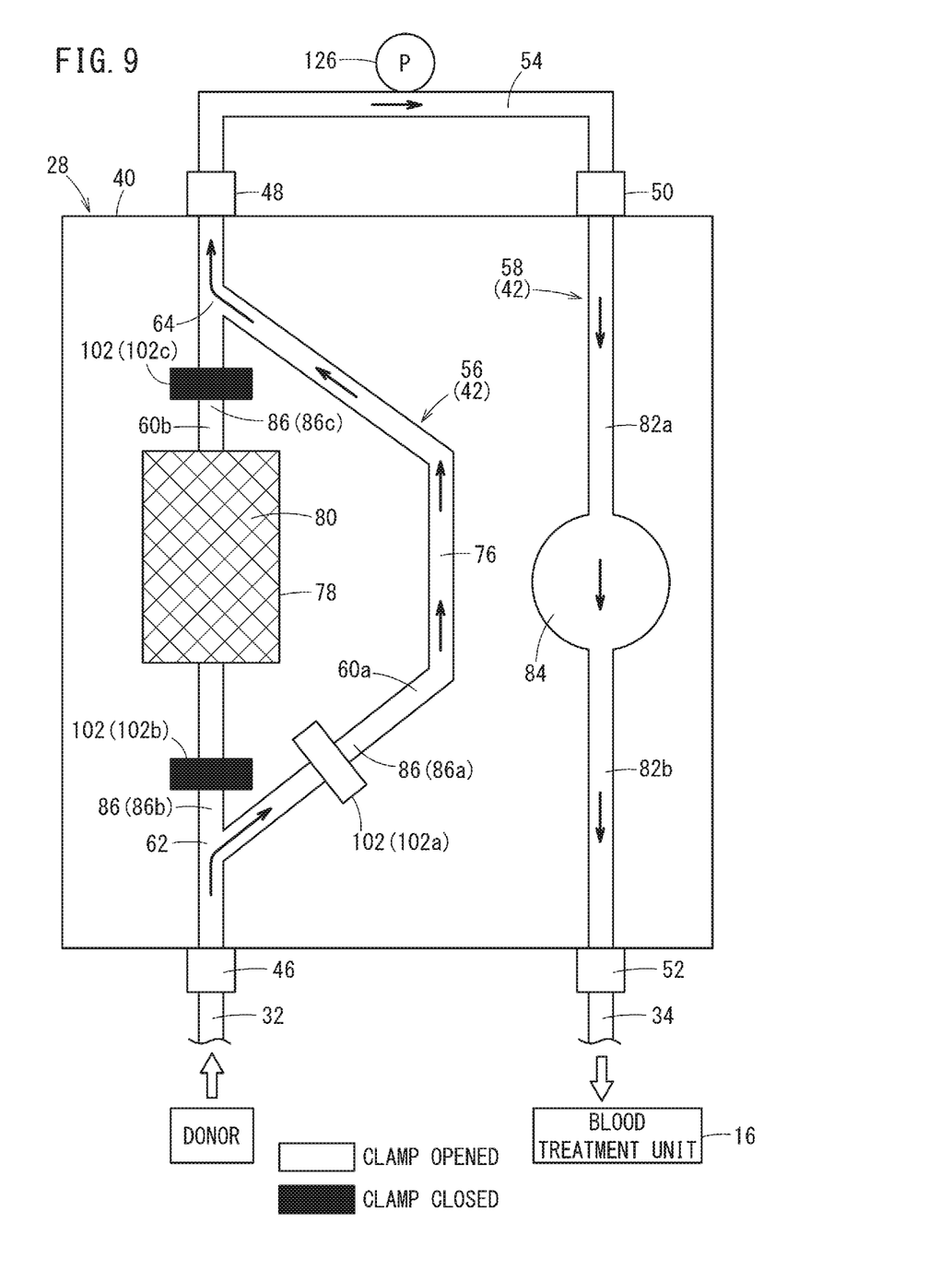
FIG. 9 is a fifth explanatory diagram illustrating the operation of clamps.

Next, when second and subsequent blood collections are carried out, as shown in FIG. 9, the clamps 102b and 102c are closed, and the clamp 102a is opened. Thus, the blood returning line 60b is closed, whereas the blood collection line 60a is opened. Accordingly, from among the blood collection line 60a and the blood returning line 60b, blood is transferred via only the blood collection line 60a to the side of (the separation processing unit 18 of) the blood treatment unit 16. Thereafter, return of the blood (see FIG.

8) is carried out again. Collection of blood and return of the blood in this manner are repeated a plurality of times.

In addition, when return of the blood is performed for the last time, as shown in FIG. 8, the clamp 102a is closed, and the clamps 102b and 102c are opened.

Next, a description will be given concerning acquisition of the circuit internal pressure of the cassette 28.

At first, before collection of blood is performed in the cassette mounted state, the reaction force acquisition unit 130 acquires the reaction force of the first applied load measurement unit 76 on the basis of the detection value of the first load measurement unit 98, together with acquiring the reaction force of the second applied load measurement unit 84 on the basis of the detection value of the second load measurement unit 100.

Figure 10A:
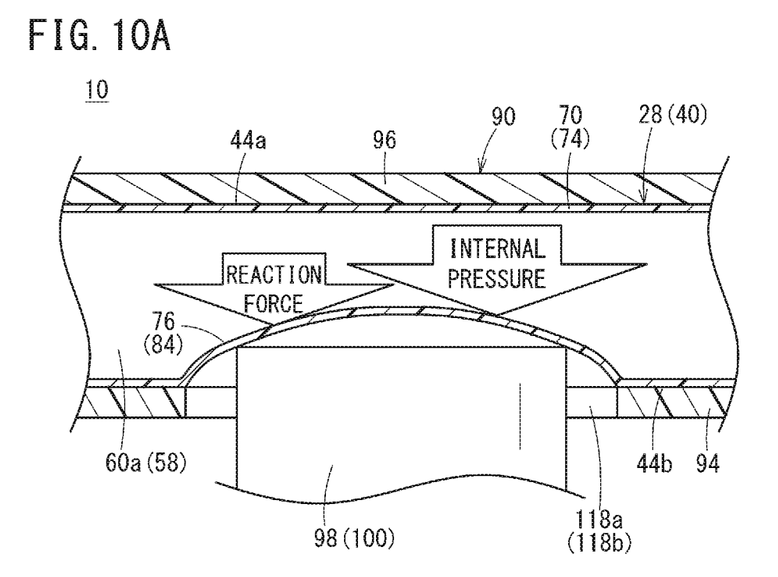
FIG. 10A is a diagram for describing load detection at a positive pressure.
Figure 10B:
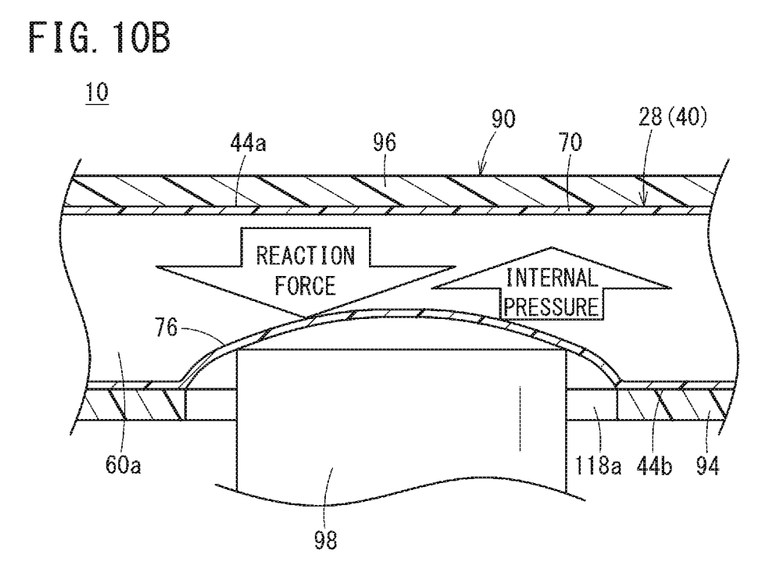
FIG. 10B is a diagram for describing load detection at a negative pressure.

Subsequently, when blood is collected by driving the pump 126, the internal pressure computation unit 132 calculates the internal pressure of the first applied load measurement unit 76. More specifically, a load, which is obtained by summing the internal pressure (circuit internal pressure) of the blood collection line 60a through which the blood flows, and the reaction force of the first applied load measurement unit 76 (the restorative force accompanying deformation of the first load measurement unit 98), is detected by the first load measurement unit 98. That is, in the case that the interior of the blood collection line 60a is at a positive pressure, as shown in FIG. 10A, the load detected by the first load measurement unit 98 (the pressing force from the first applied load measurement unit 76) is obtained simply by adding the circuit internal pressure and the reaction force. On the other hand, in the case that the interior of the blood collection line 60a is at a negative pressure, as shown in FIG. 10B, the load detected by the first load measurement unit 98 is obtained by subtracting the absolute value of the circuit internal pressure from the reaction force.

Further, when blood is collected by driving the pump 126, the internal pressure computation unit 132 calculates the internal pressure of the second applied load measurement unit 84. More specifically, a load, which is obtained by summing the internal pressure (circuit internal pressure) of the separation side line 58 through which the blood flows, and the reaction force of the second applied load measurement unit 84 (the restorative force accompanying deformation of the second applied load measurement unit 84), is detected by the second load measurement unit 100. More specifically, since the interior of the separation side line 58 is at a positive pressure, as shown in FIG. 10A, the load detected by the second load measurement unit 100 (the pressing force from the second applied load measurement unit 84) is obtained simply by adding the circuit internal pressure and the reaction force.

In this case, the blood component collection system 10 according to the present embodiment exhibits the following effects.

The biological component transfer device (cassette 28) includes the sheet-shaped device main body (cassette main body 40) in which the biological fluid line (blood line 42) is formed. The biological fluid line (blood line 42) comprises the applied load measurement unit (second applied load measurement unit 84) having the wall portion made of a soft material, and the line main body portions 82a and 82b connected to the applied load measurement unit (second applied load measurement unit 84). The apparatus (separation device 14) includes the load measurement unit (second load measurement unit 100) that measures the load applied to the wall portion of the applied load measurement unit (second applied load measurement unit 84) in the device mounted state in which the biological component transfer device (cassette 28) is attached to the apparatus (separation device 14). The applied load measurement unit (second applied load measurement unit 84) is more easily deformed than the line main body portions 82a and 82b, and is disposed at a location within the biological fluid line (blood line 42) on which only a positive pressure acts.

In accordance with such a configuration, since the applied load measurement unit (second applied load measurement unit 84) is provided in a location of the biological fluid line (blood line 42) where only a positive pressure acts, the applied load measurement unit (second applied load measurement unit 84) is not blocked or obstructed due to a negative pressure. Further, since the applied load measurement unit (second applied load measurement unit 84) is more easily deformed than the line main body portions 82a and 82b, creep deformation of the applied load measurement unit (second applied load measurement unit 84) (a reduction in the reaction force of the applied load measurement unit (second applied load measurement unit 84) over time) can be suppressed. Accordingly, the circuit internal pressure can be measured with high accuracy.

The applied load measurement unit (second applied load measurement unit 84) is formed to be wider than the line main body portions 82a and 82b.

In accordance with such a configuration, with a simple configuration, the applied load measurement unit (second applied load measurement unit 84) can be deformed more easily than the line main body portions 82a and 82b.

The apparatus (separation device 14) is a separation device 14 that separates a predetermined biological component, and further comprises a separation processing unit 18 that separates the biological component from the biological fluid, and the sampling or returning pump 126. The biological fluid line (blood line 42) includes the separation side line 58 that forms a portion of the flow path between the pump 126 and the separation processing unit 18, and the applied load measurement unit (second applied load measurement unit 84) is provided in the separation side line 58.

In accordance with such a configuration, only the positive pressure can be applied to the applied load measurement unit (second applied load measurement unit 84).

The biological fluid line (blood line 42) includes the donor side line 56 that forms a portion of the flow path between the pump 126 and the donor. The pump 126 is provided in the connection tube 54 which is made of a soft material, together with allowing the donor side line 56 and the separation side line 58 to communicate with each other.

In accordance with such a configuration, the structure of the biological component transfer system (blood component collection system 10) can be simplified.

The donor side line 56 includes the first line (blood collection line 60a) and the second line (blood returning line 60b) disposed at least partially in parallel with each other, and the first line (blood collection line 60a) includes the donor side applied load measurement unit (first applied load measurement unit 76) having the wall portion made of a soft material. The separation device 14 includes the donor side load measurement unit (first load measurement unit 98) that measures the load applied to the wall portion of the donor side applied load measurement unit (first applied load measurement unit 76) in the device mounted state. The second line (blood returning line 60b) includes the filter accommodating unit 78 in which the filter member 80 is accommodated in the interior thereof.

In accordance with such a configuration, the internal pressure of the donor side line 56 can be measured by the donor side load measurement unit (first load measurement unit 98). Further, agglomerates of the biological component (blood component) can be removed by the filter member 80.

The applied load measurement unit (second applied load measurement unit 84) is formed in a circular shape as viewed in plan, and the diameter D of the applied load measurement unit (second applied load measurement unit 84) is greater than or equal to 150% of the width W of the line main body portions 82*a* and 82*b*.

In accordance with such a configuration, it is possible to equalize the bulging caused by the increase in pressure of the applied load measurement unit (second applied load measurement unit 84), and therefore, the applied load measurement unit (second applied load measurement unit 84) can be made circular in shape as viewed in plan.

The present invention is not limited to the above-described configuration. The cassette main body 40 may be separated (detached) into a portion where the donor side line 56 is formed and a portion where the separation side line 58 is formed.

The first load measurement unit 98 and the second load measurement unit 100 may be configured in a manner so as to measure the load (in a non-contact manner) without applying pressure to the first applied load measurement unit 76 and the second applied load measurement unit 84.

The scope of application of the present invention is not limited to the blood component collection system 10, but may be applied to various systems through which a liquid is made to flow through a flow path, for example, a whole blood donation system, or a culture apparatus for various types of cells which are collected or cultured from patients or donors, or alternatively, a medicinal solution administration system, or the like. Accordingly, the liquid that flows in the biological component transfer device (biological component transfer system) is not limited to blood. The biological component transfer system may also include a form in which the biological components are allowed to flow (the biological components are circulated inside the circuit).

The biological component transfer system according to the present invention is not limited to the above-described embodiment, and it goes without saying that various modifications could be adopted therein within a range that does not depart from the essence and gist of the present invention.

The invention claimed is:

1. A biological component transfer system comprising:
    a biological component transfer device configured to be used for transferring a biological component within a biological fluids;
    a pump; and
    a separation device to which the biological component transfer device attaches;
    wherein the biological component transfer device includes a sheet-shaped device main body in which a biological fluid line is formed,
    wherein the biological fluid line comprises:
        a first load detecting portion having a wall portion; and
        a line main body portion connected to the first load detecting portion;
    wherein the separation device includes a first load detector configured to measure a load applied to the wall portion of the first load detecting portion in a state in which the biological component transfer device is attached to the separation device,
    wherein the first load detecting portion is more easily deformed than the line main body portion in a direction that is substantially perpendicular to a surface of the sheet-shaped device main body,
    wherein the biological fluid line includes a separation side line that forms a portion of a flow path between the pump and the separation device,
    wherein the first load detecting portion is in the separation side line,
    wherein the biological fluid line includes a donor side line that forms a portion of a flow path between the pump and a donor, and
    wherein the pump is located at and operates on a connection tube that connects the donor side line and the separation side line.

2. The biological component transfer system according to claim 1, wherein the first load detecting portion is formed to be wider than the line main body portion.

3. The biological component transfer system according to claim 1, wherein:
    the separation device further comprises:
        a centrifuge configured to separate the biological component from the biological fluid.

4. The biological component transfer system according to claim 3, wherein:
    the connection tube is made of a soft material.

5. The biological component transfer system according to claim 4, wherein:
    the donor side line includes a first portion and a second portion disposed at least partially in parallel with each other;
    the first portion of the donor side line includes a second load detecting portion having a wall portion;
    the separation device includes a second load detector configured to measure a load applied to the wall portion of the second load detecting portion in the state in which the biological component transfer device is attached to the separation device; and
    the second portion of the donor side line includes a filter accommodating portion in which a filter member is accommodated in an interior thereof.

6. The biological component transfer system according to claim 2, wherein:
    the first load detecting portion is formed in a circular shape as viewed from a plan view; and
    a diameter of the first load detecting portion is greater than or equal to 150% of a width of the line main body portion.

7. The biological component transfer system according to claim 2, wherein:
    the separation device further comprises:
        a centrifuge configured to separate the biological component from the biological fluid.

8. The biological component transfer system according to claim 7, wherein:
    the connection tube is made of a soft material.

9. The biological component transfer system according to claim 8, wherein:
    the donor side line includes a first portion and a second portion disposed at least partially in parallel with each other;
    the first portion of the donor side line includes a second load detecting portion having a wall portion;
    the separation device includes a second load detector configured to measure a load applied to the wall portion of the second load detecting portion in the state in which the biological component transfer device is attached to the separation device; and
    the second portion of the donor side line includes a filter accommodating portion in which a filter member is accommodated in an interior thereof.

10. The biological component transfer system according to claim 5, wherein the first portion of the donor side line, the second portion of the donor side line, and the separation side line are spaced apart from one another on the sheet-shaped device main body when viewed in a plan view.

11. The biological component transfer system according to claim 10, wherein the first portion of the donor side line is between the second portion of the donor side line and the separation side line when viewed in the plan view.

12. The biological component transfer system according to claim 1, wherein the connection tube is connected to the donor side line through a first port member of the sheet-shaped device main body, and wherein the connection tube is connected to the separation side line through a second port member of the sheet-shaped device main body.

13. The biological component transfer system according to claim 12, wherein the first port member and the second port member are on a same side of the sheet-shaped device main body.

14. The biological component transfer system according to claim 13, wherein the sheet-shaped device main body further comprises a third port member that connects to the donor and a fourth port member that connects to the separation device.

15. The biological component transfer system according to claim 14, wherein the third port member and the fourth port member are on a same side of the sheet-shaped device main body.

16. The biological component transfer system according to claim 15, wherein the third port member and the fourth port member are on a side of the sheet-shaped device main body that is opposite to the first port member and the second port member.

17. The biological component transfer system according to claim 1, wherein the separation side line includes portions that are parallel to portions of the donor side line.

* * * * *